United States Patent [19]

Wajaroff

[11] 4,177,260
[45] Dec. 4, 1979

[54] COSMETIC PREPARATIONS

[75] Inventor: Theodor Wajaroff, Darmstadt, Fed. Rep. of Germany

[73] Assignee: Wella Aktiengesellschaft, Darmstadt, Fed. Rep. of Germany

[21] Appl. No.: 784,662

[22] Filed: Apr. 5, 1977

[30] Foreign Application Priority Data

Apr. 6, 1976 [DE] Fed. Rep. of Germany ....... 2614723

[51] Int. Cl.$^2$ .......................... A61K 7/09; A61K 7/11; A61K 7/155
[52] U.S. Cl. ........................................ 424/71; 424/72; 8/160; 8/161
[58] Field of Search ...................... 8/161, 160; 424/71, 424/72

[56] References Cited

U.S. PATENT DOCUMENTS

| 2,717,228 | 9/1955 | Brown | 424/71 |
| 2,836,185 | 5/1958 | Hervey | 424/71 |
| 2,836,543 | 5/1958 | Watson | 424/71 |

FOREIGN PATENT DOCUMENTS

| 2313794 | 9/1974 | Fed. Rep. of Germany. | |
| 1197037 | 7/1970 | United Kingdom | 424/71 |
| 1197038 | 7/1970 | United Kingdom | 424/71 |

OTHER PUBLICATIONS

Chemical Abstracts: vol. 75: 17718m; vol. 58: 7066d; vol. 68: 85826a & vol. 61: 9983b.

*Primary Examiner*—Donald B. Moyer
*Attorney, Agent, or Firm*—Michael J. Striker

[57] ABSTRACT

Improved cosmetic compositions comprising aqueous preparations on the basis of keratin softening agents and also containing a swelling and penetration substance wherein as the swelling and penetration substance imidazolidinone-(2) is used.

9 Claims, No Drawings

COSMETIC PREPARATIONS

This invention relates to a cosmetic preparation on the basis of a keratin softening active material and which additionally contains as a swelling and penetration substance imidazolidinone-(2).

The activity or effectiveness of many cosmetic preparations as for instance hair shaping preparations, depilatories and various skin treatment preparations is based on the inclusion therein of an agent for softening the scleroprotein present in the hair or the skin. For this purpose, i.e. as the active scleroprotein softening agent, there are and have been utilized alkalis, mercapto compounds, sulfites or sulfides. In order to obtain a far reaching effect, i.e. satisfactory performance it has often been necessary to introduce the active agent in a relatively high concentration with the result that the cosmetic preparation is provided at or almost the extreme outermost limits of its physiological compatibility or tolerability.

Different types of active agents as for instance sulfites and the mercapto compound monothioglycolicacid-glycerinester have been utilized in preparations useful for treating hair, wherein the preparations have been adjusted to a pH value of 6 and these preparations have been used by carrying out the treatment at high temperature of over 60° C. Alkalithioglycolate which is frequently used as the active agent in depilatory preparations only achieves satisfactory results when it is used in a thioglycolic acid concentration of above 3%; it however is generally required to be present for satisfactory activity in levels of the thioglycolic acid corresponding to a concentration of 10%.

The artisan has continuously sought for means and possibilities whereby to provide for the aforesaid type of cosmetic preparations, suitable compositions and modes of applications thereof having both a desired level of activity, i.e. effectiveness and also an acceptable physiological tolerance. In this connection, it is also considered important that the aforesaid conditions be met while utilizing in the cosmetic preparations as little of the active agent as is possible and just that amount as will together with the pH value produce the best results and yet not be harmful to the hair and/or skin. The artisan has further sought to achieve the foregoing while operating with shorter working or treatment times and wherein the working or treatment can be carried out at room temperature.

In order that the preparations as herein proposed be effective to provide a strong activity the preparations have been and are formulated to contain certain auxiliary adjuvants which are conventionally designated swelling and penetration materials. These substances are able to promote the penetration of the active agent into the scleroprotein of the hair or the skin thereby favorably increasing the activity and effectiveness of the preparations.

Thus, for instance, it is possible with the use of these types of preparations to obtain satisfactory hair straightening even when such hair straightening preparation only contains a relatively low concentration of alkali lye. Further using such suitably formulated preparations, it is also possible to carry out a far reaching hair depilation or to effect removal of cornified skin layers with a short working time.

The swelling and penetration materials as heretofore used in cosmetic preparations are all possessed of different disadvantages whereby the results obtained are not always satisfactory. Further, the known substances used for swelling and penetration are either difficultly soluble in water, as for instance melamine, or are not physiologically acceptable, as for instance is the case with formamide. Other instances of materials used for these purposes as for example alkali and ammonium thiocyanate have the disadvantage that in the following oxidation treatment they undergo decomposition with the formation of undesirable byproducts or else they are relatively easily saponified as is the case with urea.

When for instance urea is used in an acid hair shaping composition on a sulfite basis (pH=6), the pH value of the composition increases during the application and use thereof by virtue of the saponification of the urea under formation of ammonium carbonate. The pH as a result rises up to 7 and even higher whereby the shaping activity of the preparation is lost. If the urea is introduced into an alkaline depilatory preparation (pH=12) on the basis of a sulfide or a mercapto compound there likewise sets in a gradual saponification of the urea under formation of ammonium carbonate, with the resultant carbonic acid formed therefrom being bound through the alkali present in the composition thereby giving rise to a decrease in the pH value and a decrease in the activity of the hair removal agent.

In accordance with the invention it has now surprisingly been found that cosmetic preparations of the aforesaid type, i.e. hair shaping, hair removal, skin treatment preparations can be obtained free of the aforesaid disadvantages but possessing the desired activity, physiological tolerability and favorable action parameters. The cosmetic preparations of the invention are characterized in that they contain as swelling and penetrating substance imidazolidinone-(2). This compound is readily water soluble, physiologically acceptable and also resistant to oxidation and saponification. In the cosmetic preparations as herein contemplated the imidazolidinone-(2) is present in an amount of about 0.5 to 30 wt. % and preferably in a concentration range of between 2 to 20 wt. %.

The content of imidazolidinone-(2) in the cosmetic preparation has the advantage that the activity of the preparation can be regulated by increasing if necessary the concentration to the upper limits of the aforesaid range without at the same time adversely affecting the physiological tolerance thereof. In addition the compositions as herein proposed possess an outstanding stability during the application and use thereof even with respect to all types of aftertreatments carried out and especially those with oxidative activity.

The cosmetic agents in accordance with the invention are especially adapted for use in permanent waving, hair straightening and depilatory preparations and in preparations which are intended for beautifying the skin. Their composition generally corresponds to that of the preparations known and customary for dressing and finishing and which are prepared on the basis of keratin softening agents. The dressing or finishing type compositions of the invention are, however, characterized in that they contain as swelling and penetrating agent imidazolidinone-(2).

Typical preparations and namely those which are useful within the frame of the instant application are further explained in the following:

The compositions which are intended for lasting or permanent shaping of the hair and namely for waving and also for straightening are preferably used in aqueous alkaline made-up preparations which contain as keratin softening active agent mercaptocarboxylic acid salts such as ammonium salts of thioglycolic acid or thiolactic acid in a concentration of about 2 to 12 wt. %. There may also be used acid adjusted waving agents and namely those preparations which have a content in an aqueous medium of an inorganic sulfite or a carboxyl group free mercapto compound such as a hydrophilic ester of thioglycolic acid. In the former case, there is preferably used sodium or ammonium sulfite in a concentration (calculated as $SO_2$) of about 3 to 8 wt. %. In the latter case, there come into consideration especially monothioglycolicacid-glycolester or -glycerinester in a concentration of about 6 to 12 wt. %. Further, aqueous alkaline hair straightening agents are used prepared on the basis of alkalis, such as sodium, potassium or lithium hydroxide which alkali is present in an amount of 2 to 8 wt. %.

The preparation in the case of waving agents are generally in the form of liquids and namely as solutions or emulsions while the straightening compositions are suitably made up as creams, gels or pastes.

For use as depilatories there come into consideration aqueous alkaline preparations which have for the most part been formulated as creams or gels. They contain as keratin softening substance an inorganic sulfide and particularly strontium sulfide or a salt of mercaptocarboxylic acid preferably an alkali or alkaline earth metal salt in concentration of about 3 to 10 wt. %.

Suitable skin treatment preparations are described in German Offenlegungsschrift No. 2,313,794 of the instant applicant. The preparations contain in an aqueous medium a sulfide, sulfite or mercapto compound as active agent and have upon formulation a pH within the range of about 6 to 13 and an active agent content of about 0.5–12 wt. %.

The cosmetic compositions of the invention can, as is readily appreciated, contain all of the conventional and known cosmetic additives such as perfume oil, wetting agents, thickeners, filler materials, alcohols, opacifiers, solvents, emulsifiers, fats, waxes, oils and the like.

The following examples are given in order to more fully illustrate the invention and are in no wise to be construed as limitative thereof.

Unless otherwise specified all of the percentages are weight percent.

EXAMPLE 1

Permanent Wave Composition on a Sulfite Basis

| | |
|---|---|
| 17.3g | aqueous solution of ammonium sulfite (34%) |
| 13.5g | sulfurous acid (5% $SO_2$ content in water) |
| 8.0g | imidazolidinone-(2) |
| 4.0g | isopropanol |
| 0.2g | perfume oil |
| 0.2g | octylphenol oxyethylated with 20 mols ethyleneoxide |
| 56.8g | water |
| 100.0g | |

The pH value of the solution amounts to 6.7.

The hair is prewet with one half of the waving liquid, is then wound up on permanent rollers and is then wet with the remaining waving liquid. The hair is then covered up with a plastic sheet and heat applied with the help of a drying hood (set at 55° C.) for 6 minutes. The hair is then rinsed with water, oxidatively fixed in the conventional manner and after treated.

EXAMPLE 2

Permanent Wave Composition on the Basis of a Thioglycolic-acidester

In that monothioglycolicacidalycerinester in water can undergo saponification in storage, it is separately packed. In preparing the waving composition, shortly before use, the ester is added to an emulsion which contains all of the other necessary components.

| | | |
|---|---|---|
| A. | 16.0g | monothioglycolicacid-glycerineester |
| B. | 5.0g | imidazolidinone-(2) |
| | 0.5g | cetylstearylalcohol |
| | 0.1g | sodium lauryl sulfate |
| | 0.6g | stearylalcohol oxyethylated with 10 mols ethyleneoxide |
| | 0.3g | perfume oil |
| | 0.5g | ammonium dihydrogenphosphate |
| | 9.30g | water |
| | 100.0g | |

A and Emulsion B are shortly before use mixed together. The pH of the resulting ready for use composition is 6.3. Prewashed and hand-towel dried hair which has been wound up on permanent wave rollers is wet through with the entire quantity of waving composition. The further treatment is then carried out as set out in Example 1.

EXAMPLE 3

Permanent Wave Composition on the Basis of Thioglycolate

| | |
|---|---|
| 18.0g | aqueous ammonium thioglycolate solution (50%) |
| 4.0g | imidazolidinone-(2) |
| 4.0g | ammoniumhydrogencarbonate |
| 0.3g | perfume oil |
| 0.5g | octylphenol oxyethylated with 20 mols ethyleneoxide |
| 73.2g | water |
| 100.0g | |

The pH of the solution amounts to 8.0.

The hair is prewet with about one-half of the waving liquid, wound up on permanent wave rollers and after wet with the remaining waving liquid. The hair is then covered over with a plastic sheet and the waving liquid allowed to work for about 10 minutes without any heating. The hair is washed out with water, oxidatively fixed in the conventional manner and after treated.

EXAMPLE 4

Permanent Wave Composition on the Basis of a Thioglycolate

A. 12.4 g addition compound of imidazolidinone-(2) and thioglycolicacid
B. 11.3 g 2-amino-2-methyl-1-propanol A and B are shortly before use dissolved in 45 ml water. The solution has a pH value of 9.2 and a concentration of free imidazolidinone-(2) of 8.6 wt. %. It is used according to the procedure described in Example 2.

Preparation of addition compound: 8.6 g Imidazolidinone-(2) are dissolved in 300 g isopropanol and then reacted with 9.2 g thioglycolicacid. The addition compound precipitates out as a fine crystalline material. The addition compound can also be prepared in the absence of a solvent by dissolving together equimolar amounts of thioglycolicacid and imidazolidinone-(2) under warming to about 95° C. and then allowing the molten material to cool. The addition compound has a melting point of 92° C.

Instead of using A, there can also be used 13.4 g of the addition compound of imidazolidinone-(2) and β-mercaptopropionic acid. The preparation of this addition compound takes place by mixing together equimolar amounts of imidazolidinone-(2) with β-mercaptopropionic acid and dissolving the mixture by heating to about 50° C. Following cooling the addition compound separates out (melting point 30° C.).

EXAMPLE 5

Depilatory Composition on the Basis of a Thioglycolate or Thiolactate

| A. | | |
|---|---|---|
| | 4.0g | calcium thioglycolate |
| | 5.0g | imidazolidinone-(2) |
| | 5.0g | calcium hydroxide |
| | 3.0g | stearylalcohol oxyethylated with 20 mols ethyleneoxide |
| | 3.0g | stearylalcohol |
| | 2.0g | vaseline |
| | 0.5g | perfume oil |
| | 77.5g | water |
| | 100.0g | |

The pH value of the cream amounts to 12.5.

| B. | | |
|---|---|---|
| | 4.6g | thiolacticacid |
| | 6.0g | imidazolidinone-(2) |
| | 8.2g | calcium hydroxide |
| | 3.0g | stearylalcohol oxyethylated with 20 mols ethyleneoxide |
| | 3.0g | stearylalcohol |
| | 2.0g | vaseline |
| | 0.5g | perfume oil |
| | 72.7g | water |
| | 100.0g | |

The pH value of the cream amounts to 12.5.

The cream is applied to the area of skin from which the hair is to be removed in a layer 1 to 2 mm in thickness. After a treatment or working time of about 2 to 5 minutes, the cream is removed and the skin thoroughly washed with water.

EXAMPLE 6

Depilatory Composition on the Basis of Strontium Sulfide

| 7.0g | powdered strontium sulfide (50% SrS content) |
|---|---|
| 10.0g | imidazolidinone-(2) |
| 3.0g | sodium sulfate (water free) |
| 2.0 g | colloidal silicic acid |
| 0.5g | perfume oil |
| 77.5g | Kaolin |
| 100.0g | |

5.0 g Of the powdery materials are shortly before use added to 5 ml water and stirred to produce a creamy paste. The pH value of this preparation amounts to 12.5. Its use is in accordance with the procedure set out in Example 5.

EXAMPLE 7

Hair Straightening Composition on the Basis of Lye

| 3.0g | Sodium hydroxide |
|---|---|
| 6.0g | imidazolidinone-(2) |
| 9.0g | cetylstearylalcohol |
| 1.0g | sodium lauryl sulfate |
| 6.0g | bentonite having a high content of montmorillonite |
| 0.3g | perfume oil |
| 74.7g | water |
| 100.0g | |

The pH value of the cream amounts to 12.6.

The cream is applied on to the curly hair and is uniformly distributed thereover. Throughout the treatment time of about 10 minutes, the hair is frequently combed smooth and then finally rinsed with water.

EXAMPLE 8

Skin Treatment Composition

| 35.0g | aqueous ammonium sulfite solution (33%, pH 6.5) |
|---|---|
| 20.0g | imidazolidinone-(2) |
| 1.5g | Tylose |
| 0.5g | perfume oil |
| 5.6g | isopropanol |
| 37.4g | water |
| 100.0g | |

The gel form preparation has a pH of 6.5.

The gel is applied on to the hands by rubbing and allowed to work thereupon for about 2 minutes. The hands are then thoroughly washed with water. The skin demonstrates a youthful appearance; it is smooth, shiny and of fresh color.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A cosmetic composition for shaping hair comprising an aqueous preparation containing (a) 2-12 wt. % of a keratin softening agent selected from the group consisting of alkali, mercapto compounds, sulfites and sulfides and (b) a nitrogen-containing swelling and penetrating agent, wherein the improvement comprises that said swelling and penetrating agent is 0.5-30 wt. % of imidazolidinone-(2).

2. A cosmetic composition for treating hair of claim 1, wherein said imidazolidinone-(2) is present in an amount of 2-20 wt. %.

3. A cosmetic composition for treating hair of claim 1, wherein said composition is a hair waving preparation.

4. A cosmetic composition for treating hair of claim 1, wherein said composition is a hair straightening preparation.

5. A cosmetic composition for treating hair of claim 1, wherein said composition is a hair waving preparation having the following composition:

| 17.3g | aqueous solution of ammonium sulfite (34%) |
|---|---|

-continued

| | | |
|---|---|---|
| 13.5g | sulfurous acid (5% SO$_2$ content in water) | |
| 8.0g | imidazolidinone-(2) | |
| 4.0g | isopropanol | |
| 0.2g | perfume oil | |
| 0.2g | octylphenol oxyethylated with 20 mols ethyleneoxide | |
| 56.8g | water | |
| 100.0g. | | |

6. A cosmetic composition for treating hair of claim 1, wherein said composition is a hair waving composition prepared by admixing just prior to use

| | | |
|---|---|---|
| A. | 16.0g | monothioglycolicacid-glycerineester |
| B. | 5.0g | imidazolidinone-(2) |
| | 0.5g | cetylstearylalcohol |
| | 0.1g | sodium lauryl sulfate |
| | 0.6g | stearylalcohol oxyethylated with 10 mols ethyleneoxide |
| | 0.3g | perfume oil |
| | 0.5g | ammonium dihydrogenphosphate |
| | 93.0g | water |
| | 100.0g. | |

7. A cosmetic composition for treating hair of claim 1, wherein said composition is a hair waving preparation having the following composition:

| | |
|---|---|
| 18.0g | aqueous ammonium thioglycolate solution (50%) |
| 4.0g | imidazolidinone-(2) |
| 4.0g | ammonium hydrogen carbonate |
| 0.3g | perfume oil |
| 0.5g | octylphenol oxyethylated with 20 mols ethyleneoxide |
| 73.2g | water |
| 100.0g. | |

8. A cosmetic composition for treating hair of claim 1, wherein said composition is a hair waving composition prepared by dissolving in 45 ml water
A. 12.4 g addition compound of imidazolidinone-(2) and thioglycolic acid
B. 11.3 g 2-amino-2-methyl-1-propanol.

9. A cosmetic composition for treating hair of claim 1, wherein said composition is a hair straightening preparation having the following composition:

| | |
|---|---|
| 3.0g | sodium hydroxide |
| 6.0g | imidazolidinone-(2) |
| 9.0g | cetylstearylalcohol |
| 1.0g | sodium lauryl sulfate |
| 6.0g | bentonite having a high content of montmorillonite |
| 0.3g | perfume oil |
| 74.7g | water |
| 100.0g. | |

* * * * *